US007572828B2

(12) United States Patent
Shoemaker et al.

(10) Patent No.: US 7,572,828 B2
(45) Date of Patent: Aug. 11, 2009

(54) IDENTIFICATION OF ANTI-HIV COMPOUNDS INHIBITING VIRUS ASSEMBLY AND BINDING OF NUCLEOCAPSID PROTEIN TO NUCLEIC ACID

(75) Inventors: Robert H. Shoemaker, Boyds, MD (US); Michael Currens, Frederick, MD (US); Alan Rein, Columbia, MD (US); Ya-Xiong Feng, Bethesda, MD (US); Hang Yuan, legal representative, Bethesda, MD (US); Robert Fisher, Sharpsburg, MD (US); Andrew Stephen, Catonsville, MD (US); Karen Worthy, Germantown, MD (US); Shizuko Sei, Bethesda, MD (US); Bruce Crise, Washington Grove, MD (US); Louis E. Henderson, Mt. Airy, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 303 days.

(21) Appl. No.: 10/528,747

(22) PCT Filed: Oct. 8, 2003

(86) PCT No.: PCT/US03/32086

§ 371 (c)(1),
(2), (4) Date: Mar. 22, 2005

(87) PCT Pub. No.: WO2004/032869

PCT Pub. Date: Apr. 22, 2004

(65) Prior Publication Data

US 2006/0263772 A1    Nov. 23, 2006

Related U.S. Application Data

(60) Provisional application No. 60/416,854, filed on Oct. 8, 2002.

(51) Int. Cl.
*A61P 31/18* (2006.01)
*C12Q 1/70* (2006.01)
*C12Q 1/68* (2006.01)
*C07F 9/00* (2006.01)
*C07F 9/92* (2006.01)
*A61K 31/29* (2006.01)

(52) U.S. Cl. .............. 514/503; 435/6; 435/5; 514/492; 556/64; 556/70

(58) Field of Classification Search .......... None
See application file for complete search history.

(56) References Cited

U.S. PATENT DOCUMENTS 4,476,314 A * 10/1984 Kuriyama et al. ......... 549/531

5,041,576 A    8/1991  Wasfi
6,001,555 A    12/1999 Henderson et al.
6,046,228 A    4/2000  Rice et al.

FOREIGN PATENT DOCUMENTS

| WO | WO 97/44064 A2 | 11/1997 |
|---|---|---|
| WO | WO 99/65871 A2 | 12/1999 |
| WO | WO 02/062333 A1 | 8/2002 |
| WO | WO 02/096412 A1 | 12/2002 |

OTHER PUBLICATIONS

Wafsi and Johnson. The redox potential of some heteropolyanions which are effective antiviral agents. Recent Res. Devel. Inorganic. Chem. 2000; 2:115-129.*
Hermans, P. Current review and clinical management of patients with primary HIV-1 infection: limits and perspectives. Biomedecine & Pharmacotherapy. vol. 55, Issue 6, Jul. 2001, pp. 301-307.*
Napier, et al. Treatment of ten cases of Kala-azar by sodium acetyl-para-aminophenyl sitbiate ("Stibenyl"). Proc. Roy. Soc. Med. 1922; 15:44-45.*
Rice, W., et al., "Inhibition of HIV-1 infectivity by zinc-ejecting aromatic C-nitroso compounds," *Nature*, 1993, vol. 361, pp. 473-475.
Rice, W., et al., "Inhibitors of HIV Nucleocapsid Protein Zinc Fingers as Candidates for the Treatment of AIDS," *Science*, 1995, vol. 270, pp. 1194-1197.
Turpin, J., et al., "Synthesis and Biological Properties of Novel Pyridinioalkanoyl Thiolesters (PATE) as Anti-HIV-1 Agents That Target the Viral Nucleocapsid Protein Zinc Fingers," *J. Med. Chem.*, 1999, vol. 42, pp. 67-86.
Vermeire, K., et al., "Anti-HIV agents targeting the interaction of gp120 with the cellular CD4 receptor," Expert Opin. Investig. Drugs, 2005, vol. 14, No. 10, pp. 1199-1212.
Yang, Q, et al., "Discovery of Small-Molecule Human Immunodeficiency Virus Type 1 Early Inhibitors That Target the gp120-Binding Domain of CD4," *Journal of Virology*, May 2005, vol. 79, No. 10, pp. 6122-6133.
Fossati, C.; "Management of human disease caused by protozoal parasites"; 1978, *Clinica Terapeutica*, vol. 87, No. 3, 1 page abstract.
Kao, Richard, Y.T. et al.; "A small-molecule inhibitor of the ribonucleolytic activity of human angiogenin that possesses antitumor activity"; 2002, *PNAS*, vol. 99, No. 15, pp. 10066-10071.
Mahato, Shashi B. et al.; "Urea Stibamine: An Improved Method of Preparation and Its Antileishmanial Activity"; 1987, *Biochemical Medicine and Metabolic Biology*, vol. 38, pp. 47-56.
Wasfi, Sadiq H. et al.; "The redox potentials of some heteropolyanions which are effective antiviral agents"; 2000, *Recent Res. Devel. Inorganic Chem.*, vol. 2, pp. 115-129.
Berenguer, Juan, et al., "Visceral leishmaniasis in patients infected with human immunodeficiency virus (HIV)," *Annals. of Internal Medicine* (1989) 111: 129-132.

(Continued)

*Primary Examiner*—Mary E Mosher
*Assistant Examiner*—Stuart W Snyder
(74) *Attorney, Agent, or Firm*—Townsend and Townsend and Crew LLP

(57) ABSTRACT

The invention provides methods and pharmaceutical compositions for inhibiting viral replication, particularly retroviral replication. The methods comprise administration of stibonic acid or diphenyl compounds that disrupt viral nucleocapsid binding to nucleic acids.

16 Claims, No Drawings

OTHER PUBLICATIONS

Laguna, Fernando, et al., "Treatment of visceral leishmaniasis in HIV-infected patients: a randomized trial comparing meglumine antimoniate with amphotericin B," *AIDS* (1999) 13(9):1063-1069.

Lopez-Velez, Rogelio, et al., "Clinicoepidemiologic characteristics, prognostic factors, and survival analysis of patients coinfected with human immunodeficiency virus and *leishmania* in an area of Madrid, Spain," *Am J. Trop. Med. Hyg.* (1998) 58(4): 436-443.

Montalban, C., et al., "Visceral leishmaniasis in patients infected with human immunodeficiency virus," *Journal of Infection* (1990) 21: 261-270.

* cited by examiner

SEQUENCE LISTING

<160> NUMBER OF SEQ ID NOS: 1

<210> SEQ ID NO 1
<211> LENGTH: 28
<212> TYPE: DNA
<213> ORGANISM: Artificial Sequence
<220> FEATURE:
<223> OTHER INFORMATION: Description of Artificial Sequence:biotinylated
      28 base oligonucleotide for viral NC-p7 protein
      association assay

<400> SEQUENCE: 1
gacttgtgga aaatctctag cagtgcat                                          28

IDENTIFICATION OF ANTI-HIV COMPOUNDS INHIBITING VIRUS ASSEMBLY AND BINDING OF NUCLEOCAPSID PROTEIN TO NUCLEIC ACID

CROSS-REFERENCES TO RELATED APPLICATIONS

This application claims benefit of U.S. provisional application No. 60/416,854, filed Oct. 8, 2002, which is herein incorporated by reference.

BACKGROUND OF THE INVENTION

It is well known that, under selection pressure, viruses often mutate to drug-resistant strains, thereby limiting the efficacy of most antiviral agents. Those viral structures that are required for viability and growth are often good drug targets because their inactivation cannot be easily overcome by mutation. The utility of these targets can be further enhanced if the structures are mutationally intolerant. Furthermore, these structures may be conserved and/or maintained between virus families, groups or genuses.

In particular retroviruses such as HIV, can become rapidly resistant to drugs used to treat the infection due to the high error rate of the reverse transcriptase enzyme responsible for transcribing its RNA genome. HIV is an example of such a hyper-mutable virus. It has diverged into two major species, HIV-1 and HIV-2, each of which has many clades, subtypes and drug resistant variations.

Strategies for coping with emergence of viral drug-resistant strains include combination drug therapies (Lange (1996) *AIDS* 10 Suppl 1:S27-S30). Drugs against different viral proteins and drugs against multiple sites on the same protein are commonly used as a strategy to overcome the adaptability of the virus. Combination therapies for retroviruses, using, e.g., protease inhibitors and nucleoside analogues, such as AZT, ddI, ddC and d4T, can become ineffectual; the virus develops complete resistance in a relatively short period of time (Birch (1998) *AIDS* 12:680-681; Roberts (1998) *AIDS* 12:453-460; Yang (1997) *Leukemia* 11 Suppl 3:89-92; Demeter (1997) *J. Acquir. Immune Defic. Syndr. Hum. Retrovirol.* 14(2):136-144; Kuritzkes (1996) *AIDS* 10 Suppl 5:S27-S31). Furthermore, no effective anti-retroviral vaccine is currently available (Bolognesi (1998) *Nature* 391: 638-639; Bangham (1997) *Lancet* 350:1617-1621).

The HIV-1 caused AIDS epidemic began about 18 years ago. Since then the number of new cases have increased over time. By the end of 1994, Pat. No. 1,025,073 AIDS cases had been reported to the WHO, with a 20% increase in the number of cases since December, 1993 (Galli (1995) *Q. J. Nucl. Med.* 39:147-155). By the year 2000, the WHO predicts that there will be 30 to 40 million cumulative HIV-1 infections in the world (Stoneburner (1994) *Acta Paediatr. Suppl.* 400:1-4).

The Gag and Gag-Pol proteins in the Retroviridae, except for Spumaviruses, contain a highly conserved zinc finger motif (CCHC) within the nucleocapsid p7 (NCp7) protein portion of the polyprotein (see definitions, below). The absolute conservation of the metal chelating cysteine and histidine residues along with other residues of the protein and its in participation in essential functions during early and late virus replication has identified this feature as an antiviral target. Mutations of the chelating residues in the zinc fingers yield a non-infectious virus. Because zinc fingers are identical in most retroviruses, reagents able to inhibit its function have the potential of being broad spectrum anti-viral therapeutic drugs. For example, it has been shown that compounds that target the zinc finger by irreversible binding and cause ejection of the zinc molecule exhibit antiviral activity (see, e.g., U.S. Pat. No. 6,001,555; Rice et al., *Nature* 361:473-475, 1993). Disulfide benzamidines were also shown to be active in acutely and chronically infected cell lines (Rice et al., *Science* 270:1194-1197, 1995), and a series of pyridinioalkanoyl thioesters were developed that had superior anti-HIV-1 activity and less toxicity compared to the disulfide benzidines (see, e.g., Turpin et al., *J. Med. Chem.* 42:67-86, 1999). A cyclic peptide that mimics several binding determinants in NC-p7 and inhibits NC-p7 annealing activities has also been designed (e.g., Druillennec et al., *Proc Natl. Acad. Sci USA* 96:4886-4891, 1999; Druillennec et al., *Bioorg Med Chem Lett* 9:627-632, 1999). More recently, a series of tricyclic compounds have been identified that inhibit binding of NC-p7 to a short oligonucleotide, $d(TG)_4$, and that have anti-HIV activity (see, e.g., Stephen et al., *Biochem. Biophys. Res. Comm.* 296:1228-1237, 2002; and WO 02/062333).

Antimony-containing oxo-metalate complexes have been disclosed that have anti-viral activity (e.g., U.S. Pat. No. 5,041,576), however these compounds are limited to antimony oxo-metalate complexes that have molybdate and tungstate moieties. The present invention now provides new methods of inhibiting viral replication using antimony compounds or diphenyl compounds that disrupt nucleocapsid/nucleic acid binding interactions.

SUMMARY OF THE INVENTION

The invention provides a method of inhibiting viral replication by administration of compounds that disrupt nucleocapsid binding to nucleic acids.

In one aspect, the invention provides a method of inhibiting replication of a virus, said method comprising:

contacting a nucleocapsid protein of the virus with a compound having the formula:

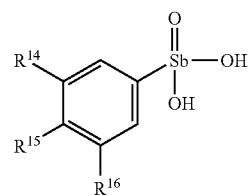

wherein $R^{14}$, $R^{15}$ and $R^{16}$ are members independently selected from H, $NO_2$, $Sb(O)(OH)_2$, $OR^7$, $SR^{17}$, CN, $NR^{17}R^{18}$, $COR^{18}$, substituted or unsubstituted alkyl and substituted or unsubstituted heteroalkyl; wherein $R^{17}$ and $R^{18}$ are members independently selected from H, $OR^{19}$, $C(O)R^{19}$, and $NR^{19}R^{20}$; wherein $R^{19}$ and $R^{20}$ are members independently selected from H, substituted or unsubstituted alkyl and substituted or unsubstituted heteroalkyl, with the proviso that at least one of $R^{14}$, $R^{15}$ and $R^{16}$ is other than H.

In one embodiment, at least one of $R^{14}$, $R^{15}$ and $R^{16}$ comprises a member selected from carboxylic acid, carboxylic acid ester, and carboxylic acid amide.

The invention also provides a method of inhibiting replication of a virus, the method comprising:

contacting a nucleocapsid protein of the virus with a compound having the formula:

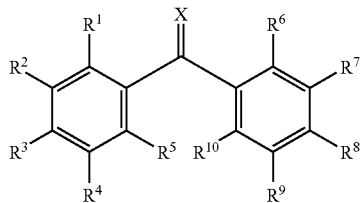

wherein $R^1$, $R^2$, $R^3$, $R^4$, $R^5$, $R^6$, $R^7$, $R^8$, $R^9$, and $R^{10}$ are members independently selected from H, substituted or unsubstituted alkyl, substituted or unsubstituted heteroalkyl, CN, $OR^{11}$, $COR^{12}$, $NR^{11}R^{13}$, and $CONR^{11}R^{13}$; wherein $R^{11}$ and $R^{13}$ are members independently selected from H, substituted or unsubstituted alkyl, and substituted or unsubstituted heteroalkyl; $R^{12}$ is a member selected from H, and $OR^{13}$; and X is a member selected from O, S, and $NR^x$; wherein $R^x$ is a member selected from H, substituted or unsubstituted alkyl and substituted or unsubstituted heteroalkyl, with the proviso that at least three of $R^1$, $R^2$, $R^3$, $R^4$, $R^5$, $R^6$, $R^7$, $R^8$, $R^9$, and $R^{10}$ are $COOR^{13}$.

In one embodiment the compound has the formula:

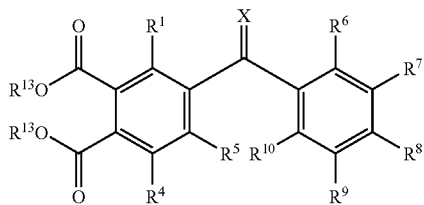

wherein at least one of $R^6$, $R^7$, $R^8$, $R^9$, and $R^{10}$ is $COOR^{13}$ and each $R^{13}$ is independently selected. In some embodiments, the compound has the formula:

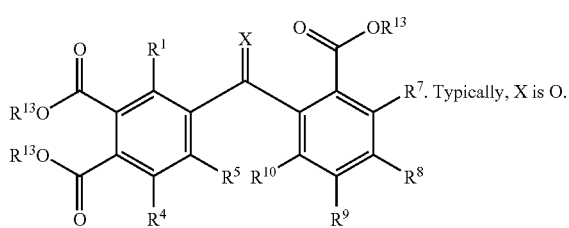

Typically, X is O.

Particular embodiments of the invention include methods wherein the virus is a retrovirus. In some embodiments, the virus is a retrovirus derived from a avian sarcoma and leukosis retroviral group, a mammalian B-type retroviral group, a human T cell leukemia and bovine leukemia retroviral group, a D-type retroviral group, a murine leukemia-related group, or a lentivirus group. Often, the virus a lentivirus. In particular embodiments, the retrovirus is an HIV-1, an HIV-2, an SIV, a BIV, an EIAV, a Visna, a CaEV, an HTLV-1, a BLV, an MPMV, an MMTV, an RSV, a FeLV, a BaEV, or an SSV retrovirus. Preferably, the retrovirus is HIV-1 or HIV-2.

In the method for inactivating a virus, the contacting of the virus with the compound can be performed in vivo. In this embodiment, the compound can be administered to inhibit the transmission of the virus. The compound can be administered intra-vaginally or intra-rectally to inhibit the transmission of the virus. The compound can be administered to a human as a pharmaceutical formulation. The compound can be administered to an animal as a veterinary pharmaceutical formulation. The method further comprises contacting the virus with an anti-retroviral agent other than an antimony compound or diphenyl compound. The anti-retroviral agent can be a nucleoside analogue, a protease inhibitor, or a non-nucleoside reverse trancriptase inhibitor (NNRTI). The nucleoside analogue can be AZT, ddCTP or DDI. The protease inhibitor can be Indinavir, Saquinavir, or Ritonavir and NNRTI include nevirapine and efavirenz.

In another aspect, the invention also provides a method for inactivating a virus, wherein the contacting of the virus with the compound can be performed in vitro. In this embodiment of the method, the contacting of the retrovirus with the compound can be performed in a blood product, blood plasma, nutrient media, protein, a pharmaceutical, a cosmetic, a sperm or oocyte preparation, cells, cell cultures, bacteria, viruses, food or drink.

In one aspect of the methods of the invention, the compound is administered to a human as a pharmaceutical formulation. Often the compound is administered intra-vaginally or intra-rectally to inhibit the transmission of the virus.

In another embodiment, the compound is administered to an animal as a veterinary pharmaceutical formulation. Preferably, the pharmaceutical formulation comprises a unit dose of a compound described herein. Often, the pharmaceutical formulation further comprises a pharmaceutical excipient.

DETAILED DESCRIPTION

The efficacy of most antiviral agents is limited because it is common that, under selection pressure, viruses mutate to drug-resistant strains. Development of drug resistance is a survival strategy particularly pronounced amongst retroviruses because of their ability to rapidly mutate. Viral structures that are required for viability and replication are typically considered as good drug targets because their inactivation cannot be easily overcome by mutation, thus often these structure are mutationally intolerant. Furthermore, these structures maybe conserved and/or maintained between virus families, groups or genera, thus providing a common target for the development of antiviral agents or therapies.

HIV-1's nucleocapsid (NC) protein, NCp7, contains two zinc fingers separated by only seven amino acids (Henderson (1992) *J. Virol.* 66:1856). Both fingers are essential for infectivity (Aldovini (1990) *J. Virol.* 64:1920; Gorelick (1990) *J. Virol.* 64:3207). Agents have been identified that target this regions, see, e.g., WO97/44064, WO99/65871, U.S. Pat. Nos. 6,001,555 and 6,046,228. The present invention employs compounds comprising an to antimony structure or diphenyl structure which bind to the nucleocapsid with high affinity and thereby inhibit interaction with nucleic acid molecules.

In a first aspect of the invention, there is provided a method of inhibiting viral replication using antimony compounds having a structure according to Formula I:

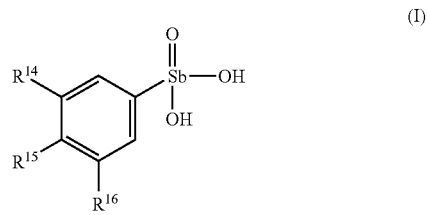

(I)

In Formula I, $R^{14}$, $R^{15}$ and $R^{16}$ are members independently selected from H, $NO_2$, $Sb(O)(OH)_2$, $OR^{17}$, $SR^{17}$, CN, $NR^{17}R^{18}$, $COR^{18}$, substituted or unsubstituted alkyl and substituted or unsubstituted heteroalkyl. $R^{17}$ and $R^{18}$ are members independently selected from H, $OR^{19}$, $C(O)R^{19}$, and $NR^{19}R^{20}$. $R^{19}$ and $R^{20}$ are members independently selected from H, substituted or unsubstituted alkyl and substituted or unsubstituted heteroalkyl. At least one of $R^{14}$, $R^{15}$ and $R^{16}$ is other than H.

In another aspect of the invention, there is provided a method of inhibiting viral replication using diphenyl compounds having a structure according to Formula II:

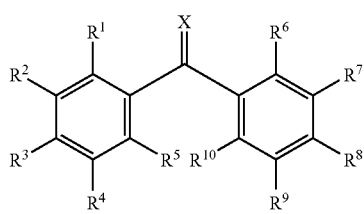

(II)

In Formula II, $R^1$, $R^2$, $R^3$, $R^4$, $R^5$, $R^6$, $R^7$, $R^8$, $R^9$, and $R^{10}$ are members independently selected from H, substituted or unsubstituted alkyl, substituted or unsubstituted heteroalkyl, CN, $OR^{11}$, $COR^{12}$, $NR^{11}R^{13}$, and $CONR^{11}R^{13}$. $R^{11}$ and $R^{13}$ are members independently selected from H, substituted or unsubstituted alkyl, and substituted or unsubstituted heteroalkyl. $R^{12}$ is a member selected from H, and $OR^{13}$; and X is a member selected from O, S, and $NR^x$. $R^x$ is a member selected from H, substituted or unsubstituted alkyl and substituted or unsubstituted heteroalkyl. At least three of $R^1$, $R^2$, $R^3$, $R^4$, $R^5$, $R^6$, $R^7$, $R^8$, $R^9$, and $R^{10}$ are $COOR^{13}$.

In another embodiment, the method of the invention utilizes compounds having a structure according to Formula III:

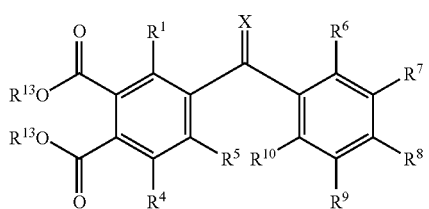

(III)

In Formula III, at least one of $R^6$, $R^7$, $R^8$, $R^9$, and $R^{10}$ is $COOR^{13}$ and each $R^{13}$ is independently selected.

In another embodiment, the compounds have a structure according to Formula IV:

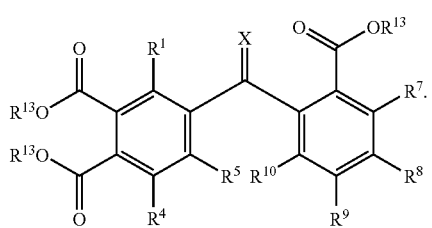

(IV)

In Formula IV, X is typically O.

The present invention is directed to the use of aromatic antimony-containing compounds and diphenyl compounds as described herein to disrupt the association of a viral nucleocapsid protein to nucleic acid. Many of these compounds are known, see, e.g., the National Cancer Institute chemical repository although none have been used as anticancer (or other indication) agents prior to the present application. Chemical structural information on some of the claimed compound is available via the DTP website: http://dtp.nci.nih.gov. Methods of synthesizing such chemicals are known to those of skill in the art. Moreover, new compounds according to Formula I, II, III, or IV that inhibit viral replication as described herein can be synthesized using techniques readily apparent to those of skill in the art. For example, antimony compounds of the invention may be prepared in accordance with the following references: Doak et al., Preparation of stibonic acids by the Scheller reaction. *J/ Am. Chem. Soc.* 1946, 68, 1987-1989. Enger & Sweeting The preparation of aromatic stibonic acids of certain benzenesulfonamides. *J. Am. Chem. Soc.* 1948, 70, 2977-2979. Reutov & Ptitsyna, Synthesis of organoantimony compounds through double diazonium salts. *Doklady Akad. Nauk S.S.S.R.* 1951, 79, 819-821. The diphenyl compounds maybe prepared, for example, in accordance with the following: Kobata et al. Manufacture of polyesters. Japan. (1978), 4pp. CODEN: JAXXAD JP 53023357 19780714 Showa. CAN 89:164360 AN 1978:564360 CAPLUS.

Definitions

To facilitate understanding the invention, a number of terms are defined below.

An "aromatic antimony-containing compound" or "antimony compound" as used herein refers to a compound having a structure corresponding to that set out in Formula I. This formula defines a three-dimensional phamacophore which interacts with the nucleocapsid protein by forming at least one hydrogen bond. Other antimony compounds to exploit the present and other hydrogen bonding modalities will be apparent to those of skill in the art.

A "diphenyl compound" as used herein refers to a compound having a structure corresponding to that set out in Formulas II, III, and IV. These formulas define a three-dimensional phamacophore which interacts with the nucleocapsid protein by forming at least one hydrogen bond. Other diphenyl compounds to exploit the present and other hydrogen bonding modalities will be apparent to those of skill in the art.

The term "aryl" means, unless otherwise stated, a polyunsaturated, aromatic, hydrocarbon substituent which can be a single ring or multiple rings (up to three rings) which are fused together or linked covalently. The term "heteroaryl" refers to aryl groups (or rings) that contain from zero to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers.

The term "alkyl," unless otherwise noted, is also meant to include those derivatives of alkyl defined in more detail below, such as "heteroalkyl." Alkyl groups which are limited to hydrocarbon groups are termed "homoalkyl".

The term "alkylene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$,—S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, and —CH=CH—N($CH_3$)—$CH_3$. Up to two heteroatoms may be consecutive, such as, for example, —$CH_2$—NH—O$CH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$R—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the aryl and heteroaryl groups are varied and are selected from, for example: halogen, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R'" and R"" are preferably independently selected from hydrogen, ($C_1$-$C_8$)alkyl and heteroalkyl, unsubstituted aryl and heteroaryl, (unsubstituted aryl)-($C_1$-$C_4$)alkyl, and (unsubstituted aryl)oxy-($C_1$-$C_4$)alkyl. When a compound of the invention includes more than one R group, for example, each of the R groups is independently selected as are each R', R", R'" and R"" groups when more than one of these groups is present.

Two of the substituents on adjacent atoms of the aryl or heteroaryl ring may optionally be replaced with a substituent of the formula -T-C(O)—(CRR'$_2$)$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-($CH_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_r$—, where s and t are independently integers of from 0 to 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted ($C_1$-$C_6$)alkyl.

Similar to the substituents described for the aryl radical, substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, and heteroalkyl, unsubstituted aryl, aryl substituted with 1-3 halogens, unsubstituted alkyl, alkoxy or thioalkoxy groups, or aryl-($C_1$-$C_4$)alkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those-derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al, "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

"Contacting" refers to the act of bringing components of a reaction into adequate proximity such that the reaction can occur. More particularly, as used herein, the term "contacting" can be used interchangeably with the following: combined with, added to, mixed with, passed over, flowed over, etc.

As used herein, the term "Gag-Pol protein" refers to the polyprotein translation product of HIV-1 or other retroviruses, as described, e.g., by Fehrmann (1997) *Virology* 235: 352359; Jacks (1988) *Nature* 331:280-283. The "Gag protein" is processed by a viral protease to yield mature viral proteins, see, e.g., Humphrey (1997) *Antimicrob. Agents Chemother.* 41:1017-1023; Karacostas (1993) *Virology* 193: 661-671.

The term "halogen" is used herein to refer to fluorine, bromine, chlorine and iodine atoms.

As used herein, "isolated," when referring to a molecule or composition, such as, for example, an antimony compound or diphenyl compound of the invention, an antimony compound- or diphenyl compound-complexed polypeptide or virus, or an antimony compound- or diphenyl compound-inactivated virus, means that the molecule or composition is separated from at least one other compound, such as a protein, other nucleic acids (e.g., RNAs), or other contaminants with which it is associated in vivo or in its naturally occurring state. Thus, a compound, polypeptide or virion is considered isolated when it has been isolated from any other component with which it is naturally associated, e.g., cell membrane, as in a cell extract, serum, and the like. An isolated composition can, however, also be substantially pure. An isolated composition can be in a homogeneous state and can be in a dry or an aqueous solution. Purity and homogeneity can be determined, for example, using analytical chemistry techniques such as polyacrylamide gel electrophoresis (SDS-PAGE) or high performance liquid chromatography (HPLC).

As used herein, the term "nucleocapsid protein" or "NC protein" refers to the retroviral nucleocapsid protein, which is an integral part of the virion nucleocapsid, where it coats the dimeric RNA genome, as described by, e.g., Huang (1997) *J. Virol.* 71:4378-4384; Lapadat-Tapolsky (1997) *J. Mol. Biol.* 268:250-260. HIV-1's nucleocapsid protein is termed "NCp7," see also Demene (1994) *Biochemistry* 33:11707-11716.

All NC proteins of the Oncovirinae and Lentivirinae subfamilies of Retroviridae contain sequences of 14 amino acids with 4 invariant residues, $Cys(X)_2Cys(X)_4His(X)_4Cys$, (L. E. Henderson et al. *J. Biol. Chem.* 256, 8400 (1981)) which chelate zinc through histidine imidazole and cysteine thiolates with a $K_d$ less than $10^{-13}$ (J. M. Berg, *Science* 232, 485 (1986); J. W. Bess, Jr., et al., *J. Virol.* 66, 840 (1992); M. R. Chance et al., *Proc. Natl. Acad. Sci. U.S.A.* 89, 10041 (1992); T. L. South and M. F. Summers, *Adv. Inorg. Biochem.* 8, 199 (1990); T. L. South, et al., *Biochem. Pharmacol.* 40, 123 (1990)). These structures are referred to as retroviral CCHC zinc fingers, and are one of the most highly conserved features of retroviruses. Examples of retroviruses which possess at least one CCHC type zinc finger per nucleocapsid protein include, but are not limited to, HIV-1, HIV-2, SIV, BIV, EIAV, Visna, CaEV, HTLV-1, BLV, MPMV, MMTV, RSV, FeLV, BaEV, and SSV.

The term "retrovirus" as used herein refers to viruses of the Retroviridae family, which typically have ssRNA transcribed by reverse transcriptase, as defined by, e.g., P. K. Vogt, "Historical introduction to the general properties of retroviruses," in Retroviruses, eds. J. M. Coffin, S. H. Hughes and H. E. Varmus, Cold Spring Harbor Laboratory Press, 1997, pp 1-26; Murphy et al. (eds.) Archives of Virology/Supplement 10, 586 pp (1995) Springer Verlag, Wien, N.Y.; and the web site for the Committee on International Taxonomy of Viruses, Virology Division of the International Union of Microbiology Society at http://www.ncbi.nlm.nih.gov/ICTV/ for viral classification and taxonomy. Retroviridae family members containing zinc finger motif-containing polypeptides and whose replication can be inhibited by the antimony compounds of the invention include avian sarcoma and leukosis retroviruses (alpharetroviruses), mammalian B-type retroviruses (betaretrovirus) (e.g., mouse mammary tumor virus), human T cell leukemia and bovine leukemia retroviruses (deltaretroviruses) (e.g., human T-lymphotropic virus 1), murine leukemia-related group (gammaretroviruses), D-type retroviruses (epsilonretrovirus) (e.g. Mason-Pfizer monkey virus), and Lentiviruses. Lentiviruses include bovine, equine, feline, ovine/caprine, and primate lentivirus groups, such as human immunodeficiency virus 1 (HIV-1). Examples of particular species of viruses whose replicative capacity is affected by the antimony compounds of the invention include HIV-1, HIV-2, SIV, BIV, EIAV, Visna, CaEV, HTLV-1, BLV, MPMV, MMTV, RSV, MuLV, FeLV, BaEV, and SSV retrovirus.

Other viruses that include proteins with zinc finger domains that interact with nucleic acid can also be targeted with the antimony compounds as described herein. For example, human papilloma virus E6 and E7 proteins contain zinc finger domains that can be targets for binding by this series of compounds (Beerheide et al. *J Natl Cancer Inst* 91:1211-20, 1999). Likewise, the hepatitis C virus genome codes -for zinc finger-containing proteins that can be targeted with the antimony compounds.

Determining Anti-Viral Activity of the Antimony and Diphenyl Compounds

In determining the anti-viral activity of an antimony compound or diphenyl compound of the invention, the ability of the compound to bind to a viral nucleocapsid protein is often evaluated. The assessment of binding affinity can be determined using techniques known by one or ordinary skill in the art (see, e.g., WO97/44064). For example tryptophan fluorescence quenching or other binding assays such as the BIAcore chip technology can be used in order to determine the binding affinity of an antimony or diphenyl compound for the viral zinc finger-containing protein. Examples of these procedures are further provided in Example 1. As appreciated by one of skill, other assay procedures can be used to provide an equivalent assessment for binding of compounds to any viral nucleocapsid protein. In some embodiments, binding affinity is assessed and compounds that bind to the nucleocapsid at a $K_D$ of less than 200 µM, determined, e.g., using a solution inhibition assay as described in the Examples, are then analyzed for anti-viral activity in vitro.

An antimony compound or diphenyl compound is within the scope of the invention if it displays any antiviral activity (i.e., any ability to decrease the cytopathic effect or diminish the transmission of or the replicative capacity of a virus). The antiviral activity can be determined empirically by clinical observation or objectively using any in vivo or in vitro test or assay, e.g., the XTT cytoprotection assay (described herein), measuring Tat-induced activity (as in the HeLa-CD4-LTR-beta-gal (MAGI cells) assay and detecting Tat-induced beta-galactosidase activity, see, e.g., Tokunaga (1998) *J. Virol.* 72:6257-6259), and the like. An antimony or diphenyl compound with any degree of measurable antiviral activity is within the scope of the invention.

One exemplary means to determine antiviral activity is with CEM-SS cells and virus (e.g., HIV-1$_{RF}$) (MOI=0.01) using the XTT (2,3-bis[2-methoxy- 4-nitro-5-sulfophenyl]-5-[(phenylamino)carbonyl]-2H-tetrazolium hydroxide) cytoprotection assay (see, e.g., Weislow, et al, *J. Natl. Canc. Inst.* 81: 577-586, 1989; Rice *PNAS* 90:9721-9724, 1993; and Rice *Antimicrob. Agents Chemother.* 41:419-426, 1997). Briefly, cells are infected with HIV-1$_{RF}$ (or other virus to be tested) in the presence of various dilutions of test compounds (antimony or diphenyl compounds and controls). The cultures are incubated for seven days. During this time control cultures without protective compounds (i.e., compounds with anti-viral activity) replicate virus, induce syncytia, and result in about 90% cell death. The cell death is measured by XTT dye reduction. XTT is a soluble tetrazolium dye that measures mitochondrial energy output, similar to MTT. Positive controls using dextran sulfate (an attachment inhibitor) or 3'-Azido -2'-3'-dideoxythymidine, AZT (a reverse transcriptase inhibitor) are added to each assay. Individual assays are done in duplicate using a sister plate method.

Effective antiviral concentrations providing 50% cytoprotection (EC$_{50}$), and cellular growth inhibitory concentrations causing 50% cytotoxicity (IC$_{50}$) are calculated.

Alternatively, any virus can be grown in culture, or in an in vivo (animal) model, in the presence or absence of an antimony compound or an antimony-containing pharmaceutical formulation to test for anti-viral, viral transmission-inhibiting activity and efficacy. Any virus, assay or animal model which would be apparent to one of skill upon review of this disclosure can be used, see, e.g., Lu (1997) *Crit. Rev. Oncog.* 8:273-291; Neildez (1998) *Virology* 243:12-20; Geretti (1998) *J. Gen. Virol.* 79:415-421; Mohri (1998) *Science* 279:1223-1227; Lee (1998) *Proc. Natl. Acad. Sci. USA* 95:939-944; Schwiebert (1998) *AIDS Res. Hum. Retroviruses* 14:269-274.

For in vitro assays, any measurable decrease in the viral load of a culture grown in the presence of an antimony or diphenyl test compound as compared to a positive or negative control compound is indicative of an anti-viral, transmission-inhibiting effect. Typically, at least a 30% reduction in viral load observed, generally, between 10% and 99%. As discussed in definition section, above, any relevant criteria can be used to evaluate the antiviral efficacy of an antimony composition or antimony-containing formulation.

Cloning and Expression of Viral Nucleocapsid Proteins

The antimony and diphenyl compounds of the invention of the invention prevent the binding of viral nucleocapsid protein to nucleic acids. In order to identify such compounds, the ability of antimony or diphenyl compounds to bind to the viral nucleocapsid is assessed in a binding assay using the targeted nucleocapsid protein, often a retroviral protein. The viral nucleocapsid proteins to detect the binding and antiviral activity of the antimony and diphenyl compounds are typically produced using-recombinant technology. General laboratory procedures for the cloning and expression of nucleocapsid proteins can be found, e.g., current editions of Sambrook, et al., Molecular Cloning *A Laboratory Manual* (2nd Ed.), Vol. 1-3, Cold Spring Harbor Laboratory, Cold Spring Harbor, N.Y., 1989; CURRENT PROTOCOLS IN MOLECULAR BIOLOGY, Ausubel, ed. Greene Publishing and Wiley-Interscience, N.Y. (1987). Sequences and sources of nucleocapsid proteins, including nucleic acids, proteins and viral sources, are publicly available, for example, through electronic databases, such as, e.g., The National Center for Biotechnology Information at http://www.ncbi.nlm.nih.gov/Entrez/, or, The National Library of Medicine at http:/fww-w.ncbi.nlm.nih.gov/PubMed/.

In general, the DNA encoding the polypeptide or peptide of interest are first cloned or isolated in a form suitable for ligation into an expression vector. After ligation, the vectors containing the DNA fragments or inserts are introduced into a suitable host cell for expression of the recombinant polypeptides. The polypeptides are then isolated from the host cells. The nucleic acids may be present in transformed or transfected whole cells, in a transformed or transfected cell lysate, or in a partially purified or substantially pure form. Techniques for nucleic acid manipulation of genes encoding zinc finger-containing proteins, such as subcloning nucleic acid sequences into expression vectors, labeling probes, DNA hybridization, and the like are described, e.g., in Sambrook and Ausubel, supra.

Once the DNAs are isolated and cloned, the desired polypeptides are expressed in a recombinantly engineered cell such as bacteria, yeast, insect, or mammalian cells. It is expected that those of skill in the art are knowledgeable in the numerous expression systems available for expression of the recombinantly produced proteins. No attempt to describe in detail the various methods known for the expression of proteins in prokaryotes or eukaryotes will be made. In brief summary, the expression of natural or synthetic nucleic acids encoding polypeptides will typically be achieved by operably linking the DNA or cDNA to a promoter (which is either constitutive or inducible), followed by incorporation into an expression vector. The vectors can be suitable for replication and integration in either prokaryotes, or eukaryotes. Typical expression vectors contain transcription and translation terminators, initiation sequences, and promoters useful for regulation of the expression of the DNA encoding recombinant polypeptides. To obtain high level expression of a cloned gene, it is desirable to construct expression plasmids which contain, at the minimum, a promoter to direct transcription, a ribosome binding site for translational initiation, and a transcription/translation terminator.

Viricidal Activity of Antimony and Diphenyl Compounds

In another aspect, the invention also provides a method of using a composition comprising a bio-organic or other material and an amount of an antimony compound of the invention effective to inactivate any virus (susceptible to inactivation by an antimonycompound) which is or may contaminate the material. The material can be bio-organic, such as, e.g., blood plasma, nutrient media, protein, a pharmaceutical, a cosmetic, a sperm or oocyte preparation, cells, cell cultures, bacteria, viruses, foods, drinks. They can be surgical or other medical materials, such as, e.g., implant materials or implantable devices (e.g., plastics, artificial heart valves or joints, collagens), medical materials (e.g., tubing for catheterization, intubation, IVs) and containers (e.g., blood bags, storage containers), and the like. Alternatively, an antimony compound of the invention can be in the form of a composition which is applied to any of the above materials as a viricidal reagent and removed before the material's use. The viricidal composition can contain a mixture of different antimony or diphenyl compounds of the invention in varying amounts. For example, antimony compounds can be added to cell cultures to reduce the likelihood of viral contamination, providing added safety for the laboratory workers.

Antimony and Diphenyl Compounds as Pharmaceutical Formulations

The invention also provides pharmaceutical formulations comprising the antimony compounds of the invention. These antimony compounds are used in pharmaceutical compositions that are useful for administration to mammals, particularly humans, for the treatment of viral, especially retroviral, infections.

The compounds of the invention can be formulated as pharmaceuticals for administration in a variety of ways. Typical routes of administration include both enteral and parenteral. These include, e.g., without limitation, subcutaneous, intramuscular, intravenous, intraperitoneal, intramedullary, intrapericardiac, intrabursal, oral, sublingual, ocular, nasal, topical, transdermal, transmucosal, or rectal. The mode of administration can be, e.g., via swallowing, inhalation, injection or topical application to a surface (e.g., eyes, mucous membrane, skin). Particular formulations typically are appropriate for specific modes of administration. Various contemplated formulations include, e.g., aqueous solution, solid, aerosol, liposomal and transdermal formulations. Details on techniques for formulation and administration are well described in the scientific and patent literature, see, e.g., the latest edition of "Remington's Pharmaceutical Sciences" (Maack Publishing Co, Easton Pa.).

Aqueous Solutions for Enteral, Parenteral or Transmucosal Administration

Examples of aqueous solutions that can be used in formulations for enteral, parenteral or transmucosal drug delivery include, e.g., water, saline, phosphate buffered saline, Hank's solution, Ringer's solution, dextrose/saline, glucose solutions and the like. The formulations can contain pharmaceutically acceptable auxiliary substances to enhance stability, deliverability or solubility, such as buffering agents, tonicity adjusting agents, wetting agents, detergents and the like. Additives can also include additional active ingredients such as bactericidal agents, or stabilizers. For example, the solution can contain sodium acetate, sodium lactate, sodium chloride, potassium chloride, calcium chloride, sorbitan monolaurate or triethanolamine oleate. These compositions can be sterilized by conventional, well-known sterilization techniques, or can be sterile filtered. The resulting aqueous solutions can be packaged for use as is, or lyophilized, the lyophilized preparation being combined with a sterile aqueous solution prior to administration.

Aqueous solutions are appropriate for injection and, in particular, for intravenous injection. The intravenous solution can include detergents and emulsifiers such as lipids. Aqueous solutions also are useful for enteral administration as tonics and administration to mucous or other membranes as, e.g., nose or eye drops. The composition can contain an antimony compound or diphenyl compound in an amount of about 1 mg/ml to 100 mg/ml, more preferably about 10 mg/ml to about 50 mg/ml.

Formulations for Enteral or Transdermal Delivery

Solid formulations can be used for enteral administration. They can be formulated as, e.g., pills, tablets, powders or capsules. For solid compositions, conventional nontoxic solid carriers can be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10%-95% of active ingredient.

A non-solid formulation can also be used for enteral (oral) administration. The carrier can be selected from various oils including those of petroleum, animal, vegetable or synthetic origin, e.g., peanut oil, soybean oil, mineral oil, sesame oil, and the like. See Sanchez, et al., U.S. Pat. No. 5,494,936. Suitable pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skin milk, glycerol, propylene glycol, water, ethanol, and the like. Nonionic block copolymers synthesized from ethylene oxide and propylene oxide can also be pharmaceutical excipients; copolymers of this type can act as emulsifying, wetting, thickening, stabilizing, and dispersing agents, see, e.g., Newman (1998) *Crit. Rev. Ther. Drug Carrier Syst.* 15:89-142.

A unit dose form, such as a tablet, can be between about 50 mg/unit to about 2 grams/unit, preferably between about 100 mg/unit to about 1 gram/unit.

Topical Administration: Transdermal/Transmucosal Delivery

Systemic administration can also be by transmucosal or transdermal means. For transmucosal or transdermal administration, penetrants appropriate to the barrier to be permeated can be used in the formulation. Such penetrants are generally known in the art, and include, e.g., for transmucosal administration, bile salts and fusidic acid derivatives. In addition, detergents can be used to facilitate permeation. Transmucosal administration can be through nasal sprays, for example, or using suppositories.

For topical administration, the agents are formulated into ointments, creams, salves, powders and gels. In one embodiment, the transdermal delivery agent can be DMSO. Transdermal delivery systems can also include, e.g., patches.

The antimony or diphenyl compounds can also be administered in sustained delivery or sustained release mechanisms, which can deliver the formulation internally. For example, biodegradeable microspheres or capsules or other biodegradeable polymer configurations capable of sustained delivery of a composition can be included in the formulations of the invention (see, e.g., Putney (1998) *Nat. Biotechnol.* 16:153-157).

Formulation Delivery by Inhalation

For inhalation, the antimony or diphenyl compound formulation can be delivered using any system known in the art, including dry powder aerosols, liquids delivery systems, air jet nebulizers, propellant systems, and the like. See, e.g., Patton (1998) *Biotechniques* 16:141-143; inhalation delivery systems by, e.g., Dura Pharmaceuticals (San Diego, Calif.), Aradigm (Hayward, Calif.), Aerogen (Santa Clara, Calif.), Inhale Therapeutic Systems (San Carlos, Calif.), and the like.

For example, the pharmaceutical formulation can be administered in the form of an aerosol or mist. For aerosol administration, the formulation can be supplied in finely divided form along with a surfactant and propellant. The surfactant preferably is soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride such as, for example, ethylene glycol, glycerol, erythritol, arabitol, mannitol, sorbitol, the hexitol anhydrides derived from sorbitol, and the polyoxyethylene and polyoxypropylene derivatives of these esters. Mixed esters, such as mixed or natural glycerides can be employed. The surfactant can constitute 0.1%-20% by weight of the composition, preferably 0.25%-5%. The balance of the formulation is ordinarily propellant. Liquefied propellants are typically gases at ambient conditions, and are condensed under pressure. Among suitable liquefied propellants are the lower alkanes containing up to 5 carbons, such as butane and propane; and preferably fluorinated or fluorochlorinated alkanes. Mixtures of the above can also be employed. In producing the aerosol, a container equipped with a suitable valve is filled with the appropriate propellant, containing the finely divided compounds and surfactant. The ingredients are thus maintained at an elevated pressure until released by action of the valve. See, e.g., Edwards (1997) *Science* 276:1868-1871.

A nebulizer or aerosolizer device for administering antimony or diphenyl compounds of this invention typically delivers an inhaled dose of about 1 mg/m$^3$ to about 50 mg/m$^3$.

Delivery by inhalation is particular effective for delivery to respiratory tissues for the treatment of respiratory conditions including an inflammatory component.

Other Formulations

In preparing pharmaceuticals of the present invention, a variety of formulation modifications can be used and manipulated to alter pharmacokinetics and biodistribution. A number of methods for altering pharmacokinetics and biodistribution are known to one of ordinary skill in the art. For a general discussion of pharmacokinetics, See, *Remington's Pharmaceutical Sciences*, supra, Chapters 37-39.

Administration

The antimony or diphenyl compounds of the invention are used in the treatment and prevention of viral infection, particularly, retroviral infections. The amount of the compound adequate to accomplish this is defined as a "therapeutically effective dose." The dosage schedule and amounts effective for this use, i.e., the "dosing regimen," will depend upon a variety of factors, including frequency of dosing, the stage of the disease or condition, the severity of the disease or condition, the general state of the patient's health, the patient's physical status, age and the like. In calculating the dosage regimen for a patient, the mode of administration also is taken into consideration.

The dosage regimen must also take into consideration the pharmacokinetics, i.e., the antimony or diphenyl compound's rate of absorption, bioavailability, metabolism, clearance, and the like (see. e.g.; the latest Remington's edition, supra).

Single or multiple administrations of the compositions can be carried out with dose levels and pattern being selected by the treating physician. In any event, the pharmaceutical formulations should pro-vide a quantity of an antimony compound or diphenyl compound sufficient to treat the patient effectively. The total effective amount of an antimony compound or diphenyl compound of the present invention can be administered to a subject as a single dose, either as a bolus or by infusion over a relatively short period of time, or can be administered using a fractionated treatment protocol, in which the multiple doses are administered over a more prolonged period of time. One skilled in the art would know that the concentration of an antimony compound or diphenyl compound of the present invention required to obtain an effective dose in a subject depends on many factors including, e.g., the pharmacokinetics of the prodrug and of its hydrolysis product, the age and general health of the subject, the route of administration, the number of treatments to be administered and the judgment of the prescribing physician. In view of these factors, the skilled artisan would adjust the dose so as to provide an effective dose for a particular use.

As appreciated by one of skill in the art, the antimony or diphenyl compounds can be used in conjunction with other therapies used for the treatment of viral infection. For example, in HIV-1 infection an antimony compound or diphenyl compound can be used in a therapeutic regimen that includes nucleoside analog therapy an protease inhibitor therapy.

Vaccine Formulations Comprising the Compounds of the Invention

In another aspect, the invention also provides an isolated and inactivated virus, where the virus is inactivated by a method comprising contacting the virus with an antimony compound or diphenyl compound of the invention, wherein contacting said virus with said compound inactivates said virus. In one embodiment the isolated and inactivated virus further comprises a vaccine formulation.

The antimony compound-complexed or diphenyl compound-complexed, inactivated viruses of the invention are used in vaccine formulations that are useful for administration to mammals, particularly humans to treat and generate immunity to of a variety of viral diseases, particularly retroviral infections, such as HIV-1. The vaccine formulations can be given single administrations or a series of administrations. When given as a series, inoculations subsequent to the initial administration are given to boost the immune response and are typically referred to as booster inoculations.

The vaccines of the invention contain as an active ingredient an immunogenically effective amount of an antimondy compound-complexed or diphenyl compound-complexed, inactivated, virus. Useful carriers are well known in the art, and include, e.g., thyroglobulin, albumins such as human serum albumin, tetanus toxoid, polyamino acids such as poly (D-lysine: D-glutamic acid), influenza, hepatitis B virus core protein, hepatitis B virus recombinant vaccine and the like. The vaccines can also contain a physiologically tolerable (acceptable) diluent such as water, phosphate buffered saline, or saline, and further typically include an adjuvant. Adjuvants such as incomplete Freund's adjuvant, aluminum phosphate, aluminum hydroxide, or alum are also advantageously used to boost an immune response.

Uses of Compound-Inactivated Viruses and Compound-Complexed Proteins

In addition to uses as vaccines, antimony compound-inactivated or diphenyl compound-inactivated viruses and antimony compound-complexed or diphenyl-complexed viral proteins have a variety of uses. For example, antimony compound-complexed or diphenyl compound-complexed viral proteins or compound-inactivated viruses can be used as reagents for the detection of corresponding anti-viral antibodies or as crystallization reagents for X-ray crystallization analysis or other ultrastructural studies, see, e.g., Yamashita (1998) *J. Mol. Biol.* 278:609-615; Wu (1998) *Biochemistry* 37:4518-4526.

Kits

In an additional aspect, the present invention provides kits embodying the methods herein. Kits of the invention optionally comprise one or more of the following: (1) a diphenyl or antimony component as described herein; (2) instructions for practicing the methods described herein, and/or for using the antimony or diphenyl component; (3) one or more assay component; (4) a container for holding the antimony or diphenyl compound, assay components, or apparatus components useful for manipulating the antimony compound or diphenyl compound or practicing the methods herein, and, (5) packaging materials.

In a further aspect, the present invention provides for the use of any compound, kit, or kit component herein, for the practice of any method or assay herein, and/or for the use of any apparatus or kit to practice any assay or method herein.

The invention will be described in greater detail by way of specific examples. The following examples are offered for illustrative purposes, and are intended neither to limit or define the invention in any manner.

EXAMPLES

Example 1

Binding of Antimony Compounds and Diphenyl Compounds to Viral Nucleocapsid Protein High-Throughput Screen A high throughput screen was used to detect small molecules that disrupted the association of viral NC-p7 protein with an oligonucleotide. The assay was performed using a Tomtec Quadra robotic system. NC protein was immobilized on Costar (Corning, N.Y.) high-bind polystyrene 96 well plates by incubating 100 µl 250 nM NC-p7 in phosphate buffered saline (PBS)/10 µM zinc chloride/10 mM β-mercaptoethanol/0.05% Tween overnight at 4° C. 200 µl of 2% BSA in PBS/10 µM zinc chloride/10 mM β-mercaptoethanol/0.05% Tween was added and incubated at room temperature for 1-2 hours in order to block the plates. The plates were then washed 2 times with 200 µl PBS/10 µM zinc chloride/10 mM β-mercaptoethanol/0.05% Tween using a Titertek M96V plate washer and stored overnight at 4° C. 5 nM biotinylated 28 base oligonucleotide (5' GACTTGTG-GAAAATCTCTAGCAGTGCAT 3') in PBS/10 µM zinc chloride/10 mM β-mercaptoethanot/0.05% Tween was added to each well followed by 10 µM of test compound (in 20% dimethyl sulphoxide) from the Diversity Set and allowed to incubate at room temperature for 1 hour. Plates were then washed 3 times with 200 µl PBS/0.05% Tween. Binding of the biotinylated 28 mer was measured by adding 100 µl 1:20000 dilution of nutravidin-horse radish peroxidase (stock 0.8 mg/ml, from Pierce Chemical Co. Rockford, Ill.) and incubating at room temperature for 1 hour. The plates were washed 3 times with 200 µl PBS/0.05% Tween. Plates were developed by adding 100 µl of Supersignal (Pierce Chemical Co. Rockford, Ill.) and bioluminescence was measured in a Wallac Victor plate reader. Each plate had eight positive (5 mM EDTA in PBS) and eight negative (20% DMSO alone) controls. The hit threshold was set at 100% inhibition. Active compounds that were identified included NSC 13778, NSC 13746, NSC 13755, and NSC 28620.

Secondary Screen

A secondary screen was used to identify small molecules that disrupt in vitro assembly of Gag precursor protein into virus-like particles. Artificial viral particles were assembled from recombinant Gag protein and tRNA as previously described (see, e.g., Campbell & Rein, "In vitro assembly properties of human immunodeficiency virus type 1 Gag protein lacking the p6 domain" *J. Virol.* 73: 2270-2279, 1999).

Two series of active compounds were identified that disrupted viral assembly. One series, an aromatic antimony-containing series, is based on the antimony-containing compound NSC 13778. The other series, a diphenyl series, is based on NSC 28620. Exemplary compounds that disrupted viral assembly in the antimony series in addition to NSC 13778 included NSC 13746, NSC 13771, NSC 13755, NSC 13759, NSC 13760, NSC 13765, and NSC 13793.

A fluorescence polarization assay was used to measure the binding between gag precursor protein and oligonucleotides. Short oligonucletoides ($d(TG)_4$) were used to monitor binding. The activity of the compounds toward gag precursor protein was assessed using a BIAcore® solution inhibition assay (e.g., Christensen et al., *Anal Biochem* 249:153-164, 1997; Fivash et al., *Curr. Opin. Biotechnol.* 9:97-101, 1998; Fisher et al., *J. Virol.* 72:1902-1909, 1998). Gag precursor protein and a $d(TG)_4$ oligonucleotides immobilized on a flow surface were incubated to allow formation of a complex. Increased amounts of the candidate compounds were then added to disrupt the complex. Dissociation constant were then calculated. Those compounds that were most effective at disrupting the gag precursor protein-$d(TG_4)$ complex were also most active in particle disassembly.

The fluorescence polarization assays was repeated substituting nucleocapsid protein for gag precursor protein in forming a complex with $d(TG)_4$. Generally, compounds that were most effective in disrupting the gag-$d(TG)_4$ complex were also the most active toward the nucleocapsid-$d(TG_4)$ complex.

To demonstrate the specificity of the compounds, a third fluorescence polarization assays was performed that assess the ability of the compounds to disrupt a complex between the tryptophan repressor protein and its cognate DNA. No compounds exhibited any activity up to 100 μM.

These experiments demonstrate that the compounds identified specifically interfered with the interaction between the nucleocapsid domain of gag precursor protein and the nucleic acid.

Cell-based Anti-HIV Activity

Cell based anti-HIV screening was performed in CEM-SS cells, using an XTT-cytoprotection assay (see, e.g., Weislow, et al, *J. Natl. Canc. Inst.* 81: 577-586, 1989; Rice *PNAS* 90:9721-9724, 1993; and Rice *Antimicrob. Agents Chemother.* 41:419-426, 1997)). Compounds were ranked as active (80-100% protection from HIV infection), moderate (50-79% protection) and inactive (0-49% protection). Generally, samples that had lower Kd's, i.e., bound tightly, were found to be active in the cell based assay. These include the diphenyl compound NSC 28620; and the antimony series compounds NSC 13778, NSC 13746, NSC 13755, NSC 13759, NSC 13760, and NSC 13765. NSC 13782 also exhibited activity in this assay.

Selected compounds were also tested for the ability to inhibit Moloney murine leukemia virus, which is a member of the gamma retrovirus family of retroviruses. The drugs were tested by performing the S+L- focus assay (Bassin et al., *Nature* 229:564-566, 1971), which is equivalent to a plaque assay, in the presence of the compound. None of the compounds exhibited an ability to inhibit murine leukemia virus replication.

Experiments with radio-labelled NSC 13778 also provided evidence for energy-dependent uptake of the compound in CEM-SS Leukemia cells. Further, exemplary experiments in mice showed that NSC 13778 is tolerated in vivo.

A summary of exemplary compound activity is provided in Table 1.

TABLE 1

| NCS # | $EC_{50}$ (μM) in vitro | disassembly VIP in vivo | p7 binding | XTT | p24 assay |
|---|---|---|---|---|---|
| 13778 | 3.8 | A | A | A | 0.11 |
| 13755 | 6.15 | A | M | A | 0.21 |
| 13759 | 1.5 | A | M | A | 0.19 |
| 13760 | 1.15 | A | M | A | 0.29 |
| 13765 | 3.75 | A | I | A | 0.41 |
| 13771 | 5.5 | A | I | I | 0.2 |
| 13793 | 3.25 | A | A | I | 0.14 |
| 13746 | 10.0 | A | A | A | not tested |

Exemplary Compounds

The series of compound comprising dihydroxy(oxido)stibino benzene derivatives exhibited several features that were associated with enhanced activity. The proper orientation of the substituents was one factor in obtaining enhanced activity. Typically, the meta orientation of the stibino group relative to the carbonyl group conferred optimal activity.

Exemplary Compounds in the Aromatic Stibonic Acid Family having Anti-Viral Activity:

The following compounds have activity in at least one of the assays of Table 1, i.e., an in vivo disassembly VIP assay, a p7 binding assay, an XTT assay, or a p24 assay.

NCS13778:

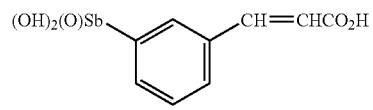

NCS13759:

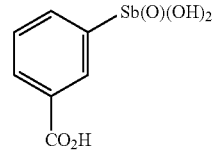

NC213760:
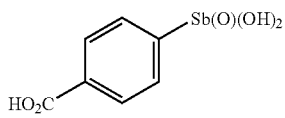

NCS13765
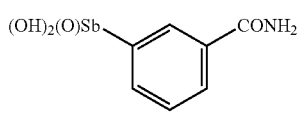

NCS13755:
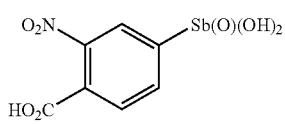

NCS13746:
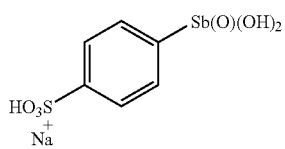

NCS13782:
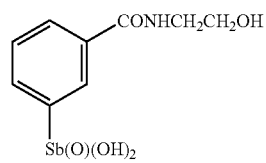

NCS13771:
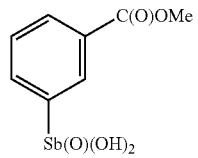

NCS13793:
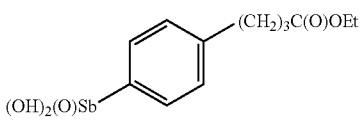

Exemplary diphenyl compound having antiviral activity:

NCS28620:
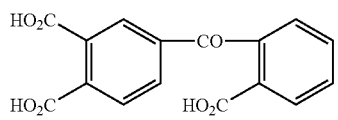

Thus, these examples showed that antimony and diphenyl compounds have been identified that disrupt in vitro assembled Gag particles. These compounds also disrupted a complex of NC-p7 or Gag precursor protein (^p6) and d(TG)4, which correlates with the particle disassembly activity. Further, host cells were protected from the cytopathic effects of HIV-1 at non-toxic doses of compounds.

All publications and patent applications cited in this specification are herein incorporated by reference as if each individual publication or patent application were specifically and individually indicated to be incorporated by reference.

What is claimed is:

1. A method of inhibiting replication of a human immunodeficiency virus, said method comprising:
contacting a nucleocapsid protein of the virus with a compound having the formula:

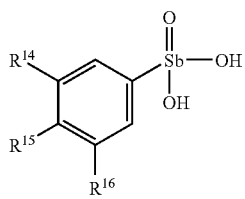

wherein
$R^{14}$, $R^{15}$ and $R^{16}$ are members independently selected from the group consisting of H, $NO_2$, $Sb(O)(OH)_2$, $OR^{17}$, $SR^{17}$, CN, $NR^{17}R^{18}$, $COR^{18}$, substituted or unsubstituted alkyl, and substituted or unsubstituted heteroalkyl
wherein
$R^{17}$ and $R^{18}$ are members independently selected from the group consisting of H, $OR^{19}$, $C(O)R^{19}$, and $NR^{19}R^{20}$
wherein
$R^{19}$ and $R^{20}$ are members independently selected from the group consisting of H, substituted or unsubstituted alkyl, and substituted or unsubstituted heteroalkyl,
with the proviso that at least one of $R^{14}$, $R^{15}$ and $R^{16}$ is other than H.

2. The method according to claim 1, wherein at least one of $R^{14}$, $R^{15}$ and $R^{16}$ comprises a member selected from the group consisting of carboxylic acid, carboxylic acid ester, and carboxylic acid amide.

3. The method of claim 1, wherein the human immunodeficiency virus is HIV-1.

4. The method according to claim 1, wherein the contacting step occurs in vivo.

5. The method according to claim 1, wherein the method further comprises contacting the virus with an anti-viral agent different from the compounds set out in claim 1.

6. The method of claim 5, wherein said anti-viral agent is a anti-retroviral agent that is a nucleotide analogue or a protease inhibitor.

7. The method of claim 6, wherein said anti-retroviral agent is a nucleotide analogue.

8. The method of claim 7, wherein the nucleotides analogue is selected from the group consisting of an AZT, a ddCTP or a DDI analogue.

9. The method of claim 6, wherein the anti-retroviral agent is a protease inhibitor.

10. The method of claim 1, wherein said compound is administered to a human as a pharmaceutical formulation.

11. The method of claim 10, wherein said compound is administered intra-vaginally or intra-rectally to inhibit the transmission of the virus.

12. A pharmaceutical formulation comprising a therapeutically effective unit dose of a compound having the formula:

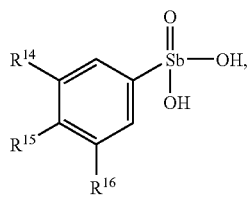

wherein
$R^{14}$, $R^{15}$ and $R^{16}$ are members independently selected from the group consisting of H, $NO_2$, $Sb(O)(OH)_2$, $OR^{17}$, $SR^{17}$, CN, $COR^{18}$, substituted or unsubstituted alkyl, and substituted or unsubstituted heteroalkyl
wherein
$R^{17}$ and $R^{18}$ are members independently selected from the group consisting of H, $OR^{19}$, $C(O)R^{19}$, and $NR^{19}R^{20}$
wherein
$R^{19}$ and $R^{20}$ are members independently selected from the group consisting of H, substituted or unsubstituted alkyl, and substituted or unsubstituted heteroalkyl,
with the proviso that at least one of $R^{14}$, $R^{15}$ and $R^{16}$ is other than H.

13. The pharmaceutical formulation of claim 12, further comprising a pharmaceutical excipient.

14. The pharmaceutical formulation of claim 12, wherein at least one of $R^{14}$, $R^{15}$ and $R^{16}$ comprises a member selected from the group consisting of carboxylic acid, carboxylic acid ester, and carboxylic acid amide.

15. The pharmaceutical formulation of claim 14, further comprising a pharmaceutical excipient.

16. The method according to claim 1, wherein $R^{14}$, $R^{15}$ and $R^{16}$ are members independently selected from the group consisting of H, $NO_2$, $Sb(O)(OH)_2$, $OR^{17}$, $SR^{17}$, CN, $COR^{18}$, substituted or unsubstituted alkyl, and substituted or unsubstituted heteroalkyl.

* * * * *

UNITED STATES PATENT AND TRADEMARK OFFICE
CERTIFICATE OF CORRECTION

PATENT NO. : 7,572,828 B2  Page 1 of 1
APPLICATION NO. : 10/528747
DATED : August 11, 2009
INVENTOR(S) : Shoemaker et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 573 days.

Signed and Sealed this

Seventh Day of September, 2010

David J. Kappos
*Director of the United States Patent and Trademark Office*